United States Patent [19]

Saito et al.

[11] Patent Number: 4,618,693

[45] Date of Patent: Oct. 21, 1986

[54] CYCLIC ORGANIC PHOSPHORUS COMPOUND AND PROCESS FOR PRODUCING SAME

[75] Inventors: Toranosuke Saito, Ibara; Masakatu Kitani, Kobe; Hiroyuki Ohishi, Ibara, all of Japan

[73] Assignee: Sanko Kaihatsu Kagaku Kenkyusho, Osaka, Japan

[21] Appl. No.: 679,720

[22] Filed: Dec. 10, 1984

[30] Foreign Application Priority Data

Dec. 9, 1983 [JP] Japan ................................. 58-231503

[51] Int. Cl.$^4$ ............................................... C07F 9/32
[52] U.S. Cl. ....................................... 558/82; 558/134
[58] Field of Search ................ 260/936, 970; 558/134, 558/82

[56] References Cited

U.S. PATENT DOCUMENTS 2,553,417  5/1951  Ladd et al. ......................... 260/970

Primary Examiner—Anton H. Sutto
Attorney, Agent, or Firm—Sughrue, Mion, Zinn, Macpeak, and Seas

[57] ABSTRACT

A cyclic organic phosphorus compound useful as a stabilizer and a fire retardant for organic substances, particularly, high molecular weight compounds is provided, which compound is expressed by the formula (I):

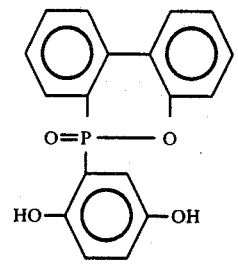

(I)

and further a process for producing the above compound (I) is provided, which process comprises reacting a compound expressed by the formula (II):

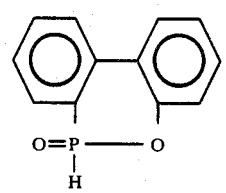

(II)

with 1,4-benzoquinone.

2 Claims, 1 Drawing Figure

CYCLIC ORGANIC PHOSPHORUS COMPOUND AND PROCESS FOR PRODUCING SAME

BACKGROUND OF THE INVENTION

This invention relates to a novel cyclic organic phosphorus compound and a process for producing the same.

Carboxylic acids derived from one of the raw materials for the compound of the present invention (a compound of the formula (II) mentioned later) is disclosed in U.S. Pat. No. 3,702,878, and esters obtained by reacting the carboxylic acids with alcohols are disclosed in U.S. Pat. Nos. 4,127,590 and 4,280,951, but the compound of the present invention has never been disclosed.

SUMMARY OF THE INVENTION

The object of the present invention is to provide a cyclic organic phosphorus compound useful as a stabilizer and a fire retardant for organic substances, particularly, higher molecular weight compounds, and a process for producing the same.

The present invention resides, in one aspect, in a cyclic organic phosphorus compound expressed by the formula (I)

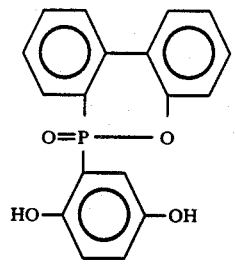
(I)

and further resides, in another aspect, in a process for producing a cyclic organic phosphorus compound expressed by the formula (I), which comprises reacting a compound expressed by the formula (II)

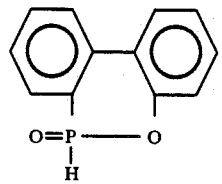
(II)

with 1,4-benzoquinone.

DETAILED DESCRIPTION OF THE INVENTION

Figure 1:
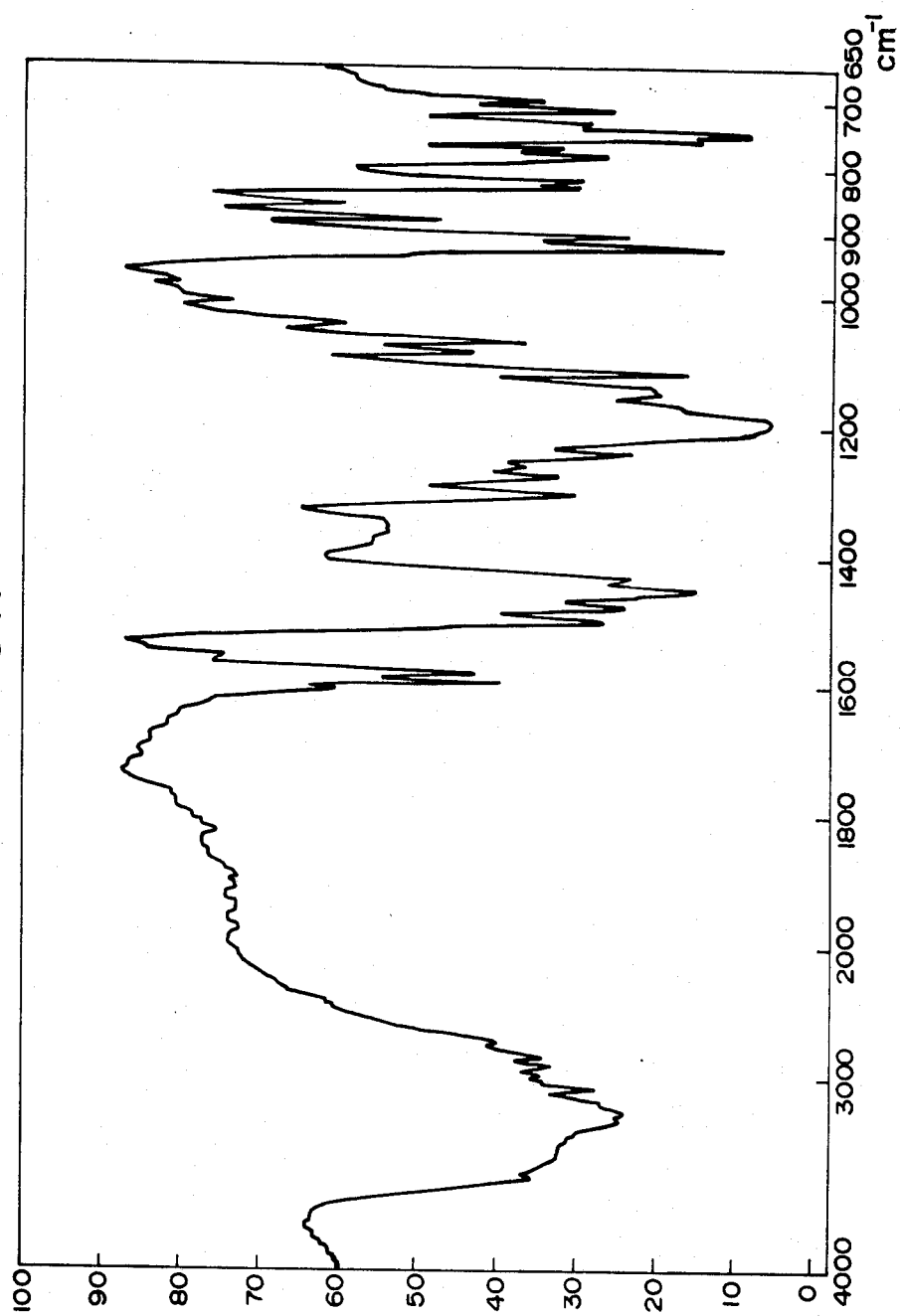
FIG. 1 shows infrared absorption spectra of the cyclic organic phosphorus compound of the present invention obtained in Example, wherein the abscissas show wavelength (cm$^{-1}$) and the ordinates show percentage transmission (%).

The compound expressed by the above formula I (hereinafter referred to as HCA-HQ) is useful as a stabilizer and a fire retardant for organic substances, particularly, higher molecular weight polymers, and for example, when it is added to homopolymers or copolymers of polyolefins, polystyrene, polyacetals, polycarbonates, polyacrylates, polyphenylene ethers, polysulfones, polyesters or epoxy resins, phenol-formaldehyde resins, etc., it notably improves their deterioration due to heat, oxygen, light, etc. and also exhibits a fire retardant effectiveness upon them.

Further since it is a bifunctional compound wherein the benzene ring linked to P of the compound has two hydroxyl groups at its p-positions, it is useful as an intermediate for various derivatives, particularly, high molecular weight compounds. For example, when it is used as a part of diol component in the production of polyester resins, polyurethane resins, etc., it exhibits superior stabilization effectiveness and fire retardance effectiveness such as resistance to solvent extraction, resistance to volatility, resistance to blooming, etc.

The compound expressed by the above formula (II) (hereinafter referred to as HCA) used as a raw material in the production of the above HCA-HQ is prepared for example by reacting o-phenylphenol with PCl$_3$ in the presence of a catalyst, hydrolyzing the resulting compound and dehydrating the resulting hydrolyzate on heating (see Japanese patent publications Nos. Sho 49-45397/1974 and Sho 50-17979/1975).

Reaction of HCA with 1,4-benzoquinone (hereinafter referred to as p-BQ) gives HCA-HQ according to the following equation:

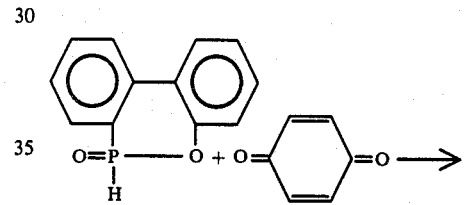

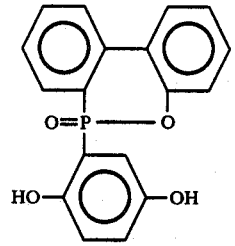

A general embodiment of the production process of the present invention will be described below.

An inert solvent and HCA are fed into a reactor equipped with a stirrer, a reflux condenser, a thermometer and a port for feeding raw material and the temperature is kept at room temperature to 100° C., preferably 50° to 80° C. When HCA has dissolved, p-BQ is added. p-BQ is used in the form of finely-divided powder or an inert solvent solution. As the inert solvent, those which dissolve the raw materials and the resulting reaction product while hot, but are slight in the solubility of the product therein while cold, are preferred, but in the case where the solubility is high, there may be applied concentration and/or deposition through addition of a solvent which does not dissolve or difficultly dissolves the material and the product. Examples of the inert solvent are ethylene glycol lower alkyl ethers, propylene glycol lower alkyl ethers, benzene, toluene, xylene, etc.

Addition of p-BQ is carried out while a state is kept wherein HCA is always present in an inert solvent in excess of an equivalent amount to that of p-BQ. If such a state is not kept, there is a high possibility of danger that the amount of byproducts formed other than the objective product increases. As for the reaction of HCA with p-BQ, any method may be employed so long as it is carried out under conditions wherein such a state is kept. For example, it is possible to add a mixture of HCA with p-BQ so that HCA can be always present in excess of the theoretical amount in respect of their proportion fed.

After completion of the addition, the mixture is reacted at 70°~150° C. for 0.5~5 hours, preferably at 120°~130° C. for 1.5~3 hours. After the reaction end point has been confirmed according to gas chromatography or liquid chromatography, the reaction mixture is cooled down to a temperature in the vicinity of room temperature, followed by filtering the precipitate, washing and drying to obtain the objective compound. As the washing solvent, the solvent used for the reaction may be used, but if its vapor pressure is low, a secondary washing may be carried out with a suitable solvent having a high vapor pressure.

The present invention will be further described by way of an Example.

EXAMPLE

HCA (540 g. 2.5 mols) was added to ethyl cellosolve (1,000 g), and the temperature of the mixture was raised to 70° C. with stirring. After HCA was completely dissolved, finely-divided powder of p-BQ (243 g, 2.25 mols) was added to the solution in small divided portions over 2 hours while the temperature was kept at 70°~90° C. After completion of the addition, the solution was kept at 125°~130° C. for 2 hours, followed by cooling it to 20° C., filtering the resulting precipitates, washing the filtered mass with ethyl cellosolve (180 ml) and then with methanol (180 ml), and drying at 90° C. under reduced pressure to obtain white crystalline powder (540 g). Yield: 74.1% based on p-BQ. M.P.: 250° C. This product was recrystallized from ethyl cellosolve to obtain a purified product having a melting point of 250° C. Its elemental analysis values were as follows:

|  | C | H | P |
|---|---|---|---|
| Observed values (%) | 66.83 | 3.96 | 9.39 |
| Calculated values (%) | 66.67 | 4.01 | 9.57 |

Further its infrared absorption spectra (according to potassium bromide tablet method) are shown in FIG. 1.

What we claim is:

1. A cyclic organic phosphorus compound expressed by the formula (I)

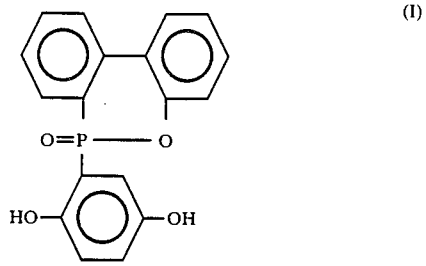

(I)

2. A process for producing a cyclic organic phosphorus compound expressed by the formula (I)

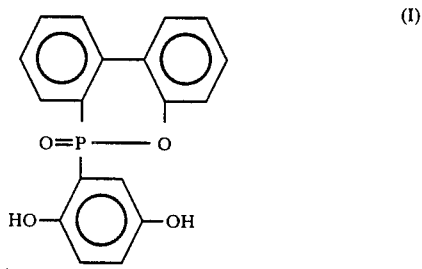

(I)

which process comprises reacting a compound expressed by the formula (II)

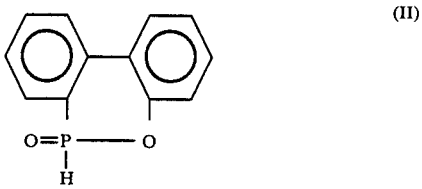

(II)

with 1,4-benzoquinone in the absence of a catalyst and wherein said compound expressed by the formula (II) is reacted with 1,4-benzoquinone while a state is kept wherein the former compound is always present in an inert solvent in excess of an equivalent amount to that of the latter compound.

* * * * *